United States Patent [19]

Heuser et al.

[11] 4,319,053
[45] Mar. 9, 1982

[54] PROCESS FOR THE PREPARATION OF 4,4'-DIHYDROXY-3,3',5,5'-TETRAALKYL-DIPHENYLALKANES

[75] Inventors: Jürgen Heuser; Günther Jeromin; Hans-Helmut Schwarz; Gerhard Friedhofen, all of Krefeld, Fed. Rep. of Germany

[73] Assignee: Bayer Aktiengesellschaft, Fed. Rep. of Germany

[21] Appl. No.: 840,896

[22] Filed: Oct. 11, 1977

Related U.S. Application Data

[63] Continuation of Ser. No. 714,786, Aug. 16, 1976, abandoned.

[30] Foreign Application Priority Data

Aug. 20, 1975 [DE] Fed. Rep. of Germany ....... 2537027

[51] Int. Cl.³ .............................................. C07C 39/16
[52] U.S. Cl. ..................................... 568/727; 568/728
[58] Field of Search ................................ 568/727, 728

[56] References Cited

U.S. PATENT DOCUMENTS 3,049,568  8/1962  Apel ..................................... 568/727
3,153,001 10/1964  Apel et al. ........................... 568/727
3,242,219  3/1966  Farnham et al. .................... 568/727
3,242,220  3/1966  Apel et al. ........................... 568/727
3,394,089  7/1968  McNutt ................................ 568/728
3,491,157  1/1970  Dietzler et al. ..................... 568/727
3,634,341  1/1972  Gammell et al. ................... 568/727
4,045,379  8/1977  Kwantes et al. .................... 568/727

OTHER PUBLICATIONS

Reinicker, "A.I.Ch.E.", vol. 20, No. 5, pp. 933–939, (1974).
"Amberlite 200, Technical Notes", Rohm & Haas Co., (Mar. 1960), Applications for Amberlite 200, ibid, (Apr. 1962).
"Dowex Fine Mesh Resins", Dow Chemical Co., Publication No. 2.

Primary Examiner—Werren B. Lone
Attorney, Agent, or Firm—Connolly and Hutz

[57] ABSTRACT

A process for the preparation of a 4,4'-dihydroxy-3,3',5,5'-tetraalkyl-diphenylalkane by reacting a 2,6-dialkyl phenol with a ketone in the presence of an acid organic ion exchanger wherein said acid ion exchanger is a macroporous resin with an average pore diameter of at least 300 Å.

8 Claims, No Drawings

PROCESS FOR THE PREPARATION OF 4,4'-DIHYDROXY-3,3',5,5'-TETRAALKYL-DIPHENYLALKANES

CROSS-REFERENCE TO RELATED APPLICATION

This application is a continuation of application Ser. No. 714,786 filed Aug. 16, 1976 and now abandoned.

This invention relates to a process for the preparation of a 4,4'-dihydroxy-3,3',5,5'-tetraalkyl-diphenylalkane, hereinafter referred to as a "tetraalkylbisphenol", by the reaction of 2,6-dialkylphenols with ketones in the presence of macroporous acid ion exchangers which have an average pore diameter of at least 300 Å.

Tetraalkylbisphenols obtained by the acid condensation of 2,6,-dialkylphenol and carbonyl compounds are valuable starting materials for the production of saponification resistant polycarbonates. The polycarbonates are obtained by the reaction of tetraalkylbisphenols with phosgene. Hydrogenation of tetraalkylbisphenols yields diols which can be reacted to produce saponification resistant polyesters.

It is known that bisphenols can be obtained by acid condensation of 2 mol of a phenol with 1 mol of a ketone (H. Schnell, H. Krimm, Angew. Chem. 14, 1963), and that strong mineral acids such as phosphoric or sulphuric acid preferably hydrochloric acid may be used for the reaction. Common to all these acids, however, is the disadvantage that they must be removed from the reaction product by complicated purification processes. Moreover, in many cases they cannot be recovered and consequently contaminate the effluent either as free acids or as their salts. Thirdly, when hydrochloric acid is used the reactors must be made of expensive materials because of the powerful corrosive action of this acid.

It has therefore been proposed, in German Auslegeschrift No. 1,242,237, to overcome these disadvantages by using as catalysts acid ion exchanger resins based on sulphonated polystyrenes cross-linked with divinyl benzene. According to the teaching given in this Auslegeschrift, the catalytic action of these exchangers depends neither on a special resin structure nor on the structure of the polymer. It is merely pointed out that a large catalyst surface promotes the reaction and, that if porous resins are used, the pores must be sufficiently large for the passage of the bisphenol molecules.

A detailed account of the relationship between the catalytic activity of the ion exchangers and their composition in the reaction described here may be found in the publication by R. A. Reiniker and B. C. Gates in A I Ch E Journal Vol. 20, No. 5, 1974, in which the formation of bisphenol is investigated, using as illustrative example the reaction of phenol with acetone in the presence of variously composed acid ion exchangers. According to this report, it is found that the catalytic activity of ion exchanger resins which are in the form of gels increases sharply with decreasing degree of cross-linking of the resin. An ion exchanger gel based on sulphonated polystyrene and cross-linked with 2% by weight of divinylbenzene, for example, is said to have twice the reaction velocity of a gel resin which has been cross-linked with 4% by weight of divinylbenzene. It is also stated that the catalytic activity of highly cross-linked, macroporous types of exchangers is distinctly lower than that of the optimum exchanger resin which is cross-linked with 2% by weight of divinylbenzene. It is stated in the report that these macroporous cross-linked exchanger resins have approximately the same activity as that of gel resins which have been cross-linked with 4% by weight of divinyl benzene, but the only experiment described with such an exchanger resin is shown to have a catalytic activity which is even lower by half than that of the gel resin cross-linked with 4% by weight of divinylbenzene.

Some experiments carried out with the reaction system of o-cresol and acetone confirm the sequence of catalytic activity of exchanger resins given by Reiniker and Gates. This sequence is therefore not an isolated case restricted to the phenol-acetone reaction system.

However, the report referred to above also states that the degree of cross-linking of the resin, expressed in terms of the divinylbenzene content, determines only the reaction velocity but not the selectivity of the reaction.

If the teaching given in the publication by Reiniker and Gates and in German Auslegeschrift No. 1,242,237 is applied to the preparation of tetraalkylbisphenols, and the condensation of 2,6-dialkylphenols and ketones is catalysed with an ion exchanger gel cross-linked with 2% by weight of divinyl benzene, it is found that extremely low conversion rates and very poor selectivities are obtained. The more highly cross-linked resins of this type have even poorer catalytic properties. The reaction velocity is in all these cases so low that economic production of these substances by ion exchanger catalysis would appear to be hardly possible.

Moreover, this method of catalysis strongly promotes the formation of unwanted indane derivatives (hereinafter referred to as "indanes") by a side reaction. Between 40 and 60% by weight of these indanes are formed, based on the quantity of tetraalkylbisphenol.

Since these indanes are very similar in their physical properties to the corresponding tetraalkylbisphenols, purification is difficult and expensive, particularly since the tetraalkylbisphenols are in many cases required to be very pure. The use of these ion exchanger resins is therefore not acceptable.

It has now surprisingly been found that a many times higher reaction velocity can be obtained if, instead of using resins in the form of gels with a low degree of cross-linkage, macroporous cross-linked acid ion exchanger resins which have an average pore diameter of at least 300 Å are used for the reaction. This effect could in no way be foreseen since, in the opinion of experts in this field, these macroporous resins have only a moderate catalytic activity comparable to that of ion exchanger gels which have been cross-linked with 4% by weight of divinyl benzene.

Particularly surprising is that this sudden increase in activity does not occur until the average pore size of the resins is increased to 300 Å in spite of the fact that, according to German Auslegeschrift No. 1,242,237, the only necessary condition to be fulfilled by the pore size is that it should be large enough to allow for the passage of the tetraalkylbisphenols, i.e. about 20 Å. One would therefore have expected to obtain a good catalytic activity even with macroporous resins of medium pore size, particularly if one takes into account that the total surface area increases with decreasing radius of the pores, which according to the aforesaid Auslegeschrift, should promote the activity of the resins. The opposite is found to be true, that is to say the reaction velocity is found to increase with increasing average pore radius.

A further increase in the degree of conversion is recorded when there is a further increase in average pore diameter in the region above 300 Å. Macroporous ion exchangers which have an average pore diameter of about 600 Å to 700 Å are found to be particularly highly reactive.

Additionally surprising was that this increase in the conversion of starting material causes entirely the formation of tetraalkylbisphenol. It is found that, in spite of the substantially higher total conversion, the formation of indane in the presence of these macroporous resins is lower than in the presence of the gel type resins. When the most effective macroporous exchangers are used, that is to say those with an average pore diameter of from 600 to 700 Å, the indane content is only from 5 to 15% by weight, based on the quantity of tetraalkylbisphenol, and is thus lower by a factor of 8 than the indane concentration produced when using ion exchanger gels with a low degree of cross-linkage or macroporous resins with an average pore diameter of less than 300 Å.

This substantial increase in the selectivity of the reaction when using ion exchangers having a particular minimum pore size was also quite unexpected since it was generally knowledge as described in German Auslegeschrift No. 1,242,237, that a particular resin structure was not necessary for the reaction.

The present invention thus relates to a process for the preparation of 4,4'-dihydroxy-3,3',5,5'-tetraalkyldiphenylalkanes by the condensation of 2,6-dialkylphenols with saturated aliphatic or cycloaliphatic ketones in the presence of acid organic ion exchangers, wherein said ion exchangers is a macroporous resin having an average pore diameter of at least 300 Å.

The process according to the invention combines an increase in the reaction velocity and an increase in yield by greatly improved selectivity and reactivity of the exchanger resins, with the known advantages of ion exchanger catalysis. Tetraalkylbisphenols can thus be produced by this method with good volume/time yields and very little loss in yield due to the formation of byproducts and can therefore be obtained as an economically useful product. The carbonyl components used may be any saturated aliphatic and cycloaliphatic ketones having from 3 to 12 and preferably 3 to 6 carbon atoms. Acetone, butanone and cyclohexanone are particularly suitable because of their ready availability.

The 2,6-dialkylphenols used are preferably those of the general formula I

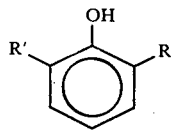

I in which R and R', which may be the same or different, represent an alkyl group having from 1 to 4 carbon atoms, e.g. a methyl, ethyl, propyl, isopropyl, butyl, tertiary butyl or isobutyl group. 2,6-Dimethylphenol is particularly preferred.

Macroporous crosslinked ion exchangers for the purpose of this invention include any ion exchangers based on sulphonated phenol formaldehyde resins. More preferably sulphonated polystyrenes which have been cross-linked with from 2 to 25% by weight, preferably from 6 to 20% by weight, of divinyl benzene, with an average pore diameter of at least 300 Å are used. Resins with pores having an average diameter of from 600 to 700 Å are particularly suitable. There are no chemical reasons for setting an upper limit for the pore diameter.

The reaction is normally carried out at atmospheric pressure but excess pressure may in some cases be an advantage for obtaining an optimum reaction temperature.

The reaction proceeds at temperatures above 50° C. Temperatures above 80° C. should be avoided because of the formation of indane derivatives, which increases with temperature. The temperature used are preferably within the range of from 50° to 80° C.

The molar ratio of 2,6-dialkylphenol to ketone should be at least 2:1. There is no upper limit to the molar ratio for any chemical reason. The optimum ratio depends on the reactivity of the reactants, the reaction temperature and the reaction time. The ratio should normally not exceed 40:1.

Sulphur compounds such as β-mercaptopropionic acid may be added as cocatalysts.

The reaction may be carried out in the presence of solvent. The solvents should be non-polar, e.g. aliphatic or aromatic hydrocarbons such as toluene, benzene or hexane, because polar compounds such as alcohols, ethers or water reduce the activity of the resins.

The addition of solvents can prevent crystallisation of the tetraalkylbisphenols in the reaction solution even when a slight excess of 2,6-dialkylphenol is used.

The process may be carried out intermittently or continuously. A continuous process may be carried out in a fluidised or solid bed reactor, preferably in the latter.

The tetraalkylbisphenol obtained is isolated from the reaction solution by known methods such as crystallisation or precipitation and the pure tetraalkylbisphenol is used for the production of polycarbonates by the reaction with phosgene in accordance with German Offenlegungsschrift No. 2,063,050 corresponding to U.S. Pat. No. 3,879,348.

EXAMPLE 1

5 Mol of 2,6-dimethylphenol, 1 mol of acetone, 1% by weight of β-mercaptopropionic acid and 30% by weight of toluene (weight of toluene based on the total weight of the solution) were reacted together for 6 hours at 70° C. in the presence of various ion exchanger resins. The ion exchangers were anhydrous and had differing compositions and structures as shown in Table 1. The quantity of catalyst used was 10% by weight, based on the total weight of the solution.

TABLE 1

| Structure and composition of the ion exchanger resins based on sulphonated polystyrenes | | | | | | |
|---|---|---|---|---|---|---|
| Exchanger No. | 1 | 2 | 3 | 4 | 5 | 6 |
| Divinyl benzene content % | 2 | 5 | 8 | 12 | 8 | 18 |
| Macroporous | no | no | no | yes | yes | yes |
| Average pore size Å | — | — | — | 160–200 | 410–480 | 620–650 |
| Total surface area mg²/g | — | — | — | 45 | 18–23 | 39–40 |
| gel characteristics | yes | yes | yes | no | no | no |

A sample was taken from each exchanger after 6 hours and investigated gas chromatographically for its 2,6-dimethylphenol, 2,2-bis-(4-hydroxy-3,5-dimethylphenyl)-propane and indane derivative content. Table 2 shows the yield after a reaction time of 6 hours.

TABLE 2

Yields of tetramethylbisphenol A and "indane" after a reaction time of 6 hours in the presence of the various catalysts according to table 1.

| Exchanger No. | 1 | 2 | 3 | 4 | 5 | 6 |
|---|---|---|---|---|---|---|
| 2,6-Dimethylphenol % by wt. | 94.3 | 93.5 | 99 | 99 | 86.1 | 80.6 |
| Tetramethylbisphenol A % by wt. | 4.0 | 4.0 | 0.1 | 0.3 | 12.0 | 18.0 |
| "Indane" % by wt. | 1.7 | 2.5 | 0.06 | 0.1 | 1.0 | 1.4 |
| Average pore size Å | gel | gel | gel | 160–200 | 410–480 | 620–656 |

Tetramethylbisphenol A was precipitated from the solution by cooling and recrystallised from toluene to yield the pure substance.

EXAMPLE 2

2,6-Dimethylphenol and butanone were reacted as indicated in Example 1. Table 3 shows the yield of 2,2-bis-(4-hydroxy-3,5-dimethylphenyl)-butane and the corresponding indane derivative.

| Exchanger No. | 1 | 2 | 3 | 4 | 5 | 6 |
|---|---|---|---|---|---|---|
| 2,6-Dimethylphenol % by wt. | 92.3 | 90.4 | 99 | 98.8 | 93.1 | 87.4 |
| Tetramethylbisphenol B % by wt. | 5.4 | 5.9 | 0.2 | 0.5 | 5.7 | 11 |
| "Indane" % by wt. | 2.3 | 3.7 | 0.2 | 0.7 | 1.2 | 1.6 |
| Average pore size Å | gel | gel | gel | 160–200 | 410–480 | 620–650 |
| Divinylbenzene content % | 2 | 4 | 8 | 12 | 8 | 18 |

The reaction products were processed in a similar manner to Example 1.

COMPARISON EXAMPLE o-Cresol and acetone were reacted as in Example 1. Table 4 shows the yield of 2,2-bis-(4-hydroxy-3-methylphenyl)-propane.

TABLE 4

Yield of bis-cresol A after a reaction time of 6 hours when using various acid ion exchanger catalysts based on sulphonated polystyrene

| Exchanger No. | 1 | 2 | 3 | 4 | 5 | 6 |
|---|---|---|---|---|---|---|
| Biscresol A % by weight | 30 | 25 | 1.1 | 4.4 | 23 | 9 |
| average pore size Å | gel | gel | gel | 160–200 | 410–480 | 620–650 |
| Divinylbenzene content % | 2 | 4 | 8 | 12 | 8 | 18 |

EXAMPLE 3

Preparation of tetramethylbisphenol A was carried out continuously in a solid bed reactor. The reaction tube had a length of 1000 mm and a diameter of 40 mm. The tube was heated to 65° C. by means of a thermostatically controlled heating jacket. It was filled with 1 liter of the anhydrous ion exchanger No. 6 shown in Table 1. 100 ml of reaction solution were pumped through the tube per hour. When entering the reactor, the reaction solution had the following composition.

| Dimethylphenol | 97.6 | % by weight |
|---|---|---|
| Acetone | 2.3 | % by weight |
| β-mercaptopropionic | 0.1 | % by weight |

The following composition was found at the outlet of the reactor:

| Dimethylphenol | 89.84 | % by weight |
|---|---|---|
| Acetone | 0.48 | % by weight |
| H$_2$O | 0.56 | % by weight |
| Tetramethylbisphenol A | 9.12 | % by weight |
| β-mercaptopropionic acid | 0.1 | % by weight |

The product was processed in a similar manner to Example 1.

What we claim is:

1. A process for preparing 4,4'dihydroxy-3,3',5,5' tetraalkyl-diphenylalkane which comprises reacting a 2,6-dialkyl phenol having from 1 to 4 carbon atoms in each alkyl moiety with a saturated aliphatic or cycloaliphatic ketone having from 3–12 carbon atoms at a molar ratio of 2,6-dialkylphenol to ketone of at least 2:1 and at a temperature of at least 50° C. in the presence of a catalytic amount of catalyst consisting of macroporous sulphonated polystyrene cross-linked with from 2 to 25% by weight of divinyl benzene and having an average pore diameter of at least 300 Å.

2. The process of claim 1 wherein said average pore diameter is from 600 to 700 Å.

3. The process of claim 1 wherein the ketone has from 3 to 6 carbon atoms.

4. The process of claim 1 wherein said ketone is acetone, butanone or cyclohexanone.

5. The process of claim 1 wherein the 2,6-dialkylphenol is 2,6-dimethylphenol.

6. The process of claim 1 wherein said ion exchange resin is a sulphonated polystyrene resin which has been cross-linked with from 6 to 20% by weight of divinylbenzene.

7. The process of claim 1 wherein said temperature is from 50° to 80° C.

8. The process of claim 1 wherein the molar ratio of 2,6-dialkylphenol to ketone does not exceed 40:1.

* * * * *